United States Patent
Rothfuss et al.

(10) Patent No.: US 8,437,525 B2
(45) Date of Patent: May 7, 2013

(54) METHOD AND SYSTEM FOR USING A MODIFIED ORDERED SUBSETS SCHEME FOR ATTENUATION WEIGHTED RECONSTRUCTION

(75) Inventors: Harold E. Rothfuss, Knoxville, TN (US); Vladimir Y. Panin, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 261 days.

(21) Appl. No.: 13/072,810

(22) Filed: Mar. 28, 2011

(65) Prior Publication Data

US 2012/0250965 A1  Oct. 4, 2012

(51) Int. Cl.
G06K 9/00 (2006.01)
A61B 6/00 (2006.01)

(52) U.S. Cl.
USPC .............................. 382/131; 382/275; 378/4

(58) Field of Classification Search .................. 302/100, 302/103, 106–107, 128, 129, 130, 131, 132, 302/133, 134, 199, 232, 254, 274, 275–276, 302/291, 305, 312; 378/4, 8, 9, 21; 600/407, 600/427
See application file for complete search history.

(56) References Cited

U.S. PATENT DOCUMENTS

| | | | |
|---|---|---|---|
| 6,856,666 B2 * | 2/2005 | Lonn et al. | 378/8 |
| 7,583,779 B2 * | 9/2009 | Tkaczyk et al. | 378/4 |
| 7,603,165 B2 * | 10/2009 | Townsend et al. | 600/427 |
| 7,813,783 B2 * | 10/2010 | Thomas et al. | 600/407 |
| 7,885,375 B2 * | 2/2011 | Bernard De Man et al. | 378/9 |
| 2012/0213424 A1 * | 8/2012 | Flohr et al. | 382/131 |

OTHER PUBLICATIONS

H. M. Hudson and R. S. Larkin, "Accelerated Image Reconstruction using Ordered Subsets of Projection Data", IEEE Transactions on Medical Imaging, vol. 13, No. 4, pp. 601-609,1994.
C. Comtat et al, "OSEM-3-D reconstruction strategies for the ECAT HRRT," IEEE NSS MIC Conf. Rec., 2004.
V. Y. Panin et al., "Fully 3-D Reconstruction with System Matrix Derived from Point Source Measurements", IEEE Transaction on Medical Imaging, vol. 25, No. 7, pp. 907-921, 2007.
J. Hamill et al., "A 68Ge PET Hot-Sphere Phantom with no Cold Shells", IEEE NSS-MIC Conference Record, 2005.
M. Casey, "Improving PET With HD PET + Time of Flight", Siemens White Paper, 2008, http://www.medical.siemens.com/siemens/en_GB/gg_nm_FBAs/files/brochures/2008/ultraHD-PET_White_Paper.pdf.

* cited by examiner

*Primary Examiner* — Seyed Azarian
(74) *Attorney, Agent, or Firm* — Peter Kendall (57) ABSTRACT

A method and system is provided for performing medical imaging. The method and system includes at least one radiation detector to detect radiation from a subject, and an image processor which determines attenuation paths for an image point, groups substantially similar attenuation path lengths for the same image point to form a modified subset group, and processing image data using the modified subset group in order to provide a reconstructed image substantially similar to an original image.

18 Claims, 9 Drawing Sheets

METHOD AND SYSTEM FOR USING A MODIFIED ORDERED SUBSETS SCHEME FOR ATTENUATION WEIGHTED RECONSTRUCTION

FIELD OF THE INVENTION

The present invention relates generally to imaging systems. More specifically, the present invention relates to methods and systems for performing image reconstruction.

BACKGROUND

Medical imaging is one of the most useful diagnostic tools available in modern medicine. Medical imaging allows medical personnel to non-intrusively look into a living body in order to detect and assess many types of injuries, diseases, conditions, etc. Medical imaging allows doctors and technicians to more easily and correctly make a diagnosis, decide on a treatment, prescribe medication, perform surgery or other treatments, and the like.

There are medical imaging processes of many types and for many different purposes, situations, or uses. They commonly share the ability to create an image of a bodily region of a patient, and can do so non-invasively. Examples of some common medical imaging types are positron emission tomography (PET), single photon emission computed tomography (SPECT), electron-beam X-ray computed tomography (CT), magnetic resonance imaging (MRI), and ultrasound (US).

Each imaging modality has specific benefits, limitations and uses and falls into a specific category such as nuclear medicine. For example x-rays are typically employed in imaging hard substances such as bone and teeth.

Nuclear medicine imaging employs a source of radioactivity to image a patient. Typically, a radiopharmaceutical is injected into the patient. Radiopharmaceutical compounds contain a radioisotope that undergoes gamma-ray decay at a predictable rate and characteristic energy. One or more radiation detectors are placed adjacent to the patient to monitor and record emitted radiation. Sometimes, the detector is rotated or indexed around the patient to monitor the emitted radiation from a plurality of directions. Based on information such as the detected position and energy, the radiopharmaceutical distribution in the body is determined and an image of the distribution is reconstructed to study the circulatory system, radiopharmaceutical uptake in selected organs or tissue, and the like.

Using these or other imaging types and associated machines, an image or series of images may be captured. Other devices may then be used to process the image in some fashion. Finally, as previously discussed, a doctor or technician may read the image in order to provide a diagnosis.

Certain applications of these imaging modalities require high-resolution images of a targeted field of view (FOV) that is less than the scan FOV for the imaging system. For example, in cardiac imaging, a high-resolution image of a small sub-region of the patient's anatomy may be desired. In emission tomography, e.g., PET or SPECT, the measured projection data contains activity from outside this targeted FOV. While reconstruction of this targeted FOV is generally straightforward for analytical reconstruction algorithms (such as filtered back projection), iterative reconstruction techniques typically require that the targeted FOV include the entire region of support of the image. This is because iterative reconstruction techniques attempt to match the estimated projection data (derived from forward projection of an estimated image) to the measured projection data. If the estimated projection data does not support the signal from outside the targeted FOV, the estimated projection data cannot correctly match the measured projection data.

In general, the signal from outside the targeted FOV should be accounted for in the image reconstruction. If the signal from outside the targeted FOV is not accounted for, the entire signal from outside the targeted FOV will be assigned to the periphery of the targeted FOV. However, this approach may result in a visible artifact at the periphery of the reconstructed image and quantitatively inaccurate regions throughout the reconstructed image.

In other cases, when a targeted FOV less than the scan FOV is requested, the full scan FOV may be reconstructed at high resolution. Subsequently, the image for the desired targeted FOV may be extracted from this image for the full scan FOV.

Specifically, in the iterative reconstruction technique, an estimate of the reconstructed volume of image data is forward projected onto the plane of the detector. The forward projected data is compared to the measured projection data. If the estimate of the reconstructed image were perfect, these two projections of data would match and there would be no difference. However, as the image is being built, there typically is a difference or error. The error or its inverse is then back-projected into the image volume to correct the volumetric image and create a new estimate for the next iteration.

More specifically, the iterative reconstruction process continues until the measured and forward projected data sets match within an acceptable error. If the iterative process is run for too long, it can start to degenerate the reconstructed image as well as being computationally expensive in terms of resource and time. One technique is to filter the measured data or at a point during a reconstruction or filter the reconstruction images. While such filtering helps to reduce noise in an image, it also reduces image resolution.

Ordered subsets are widely used for reducing the computational burden of iterative reconstruction algorithms. However, this approach should be used carefully, as the results are not proven to achieve the Maximum Likelihood estimate. Typically, Ordered Subset Expectation Maximization (OSEM) is used for image reconstruction. The reconstruction method includes resolution modeling, along with standard normalization, scatter, and attenuation corrections.

Using conventional subset selection in reconstruction algorithms produces noticeable artifacts in the transaxial views of the image. These artifacts can be strong enough to propagate to artifacts in the axial views of the images. Some artifacts have origins in the number of subsets used. By selecting a subset that results in a whole number factor of the block periodicity, an azimuthally periodic block structure artifact appears in the image.

Other types of image artifacts are independent of the selection of subset numbers used. One such artifact is the stretching of small size hot regions in the tangential direction with respect to the closest object boundary point in the transaxial view of the object. Another example is structuring of the noise in uniform background areas, which appear as rings.

Figure 1:
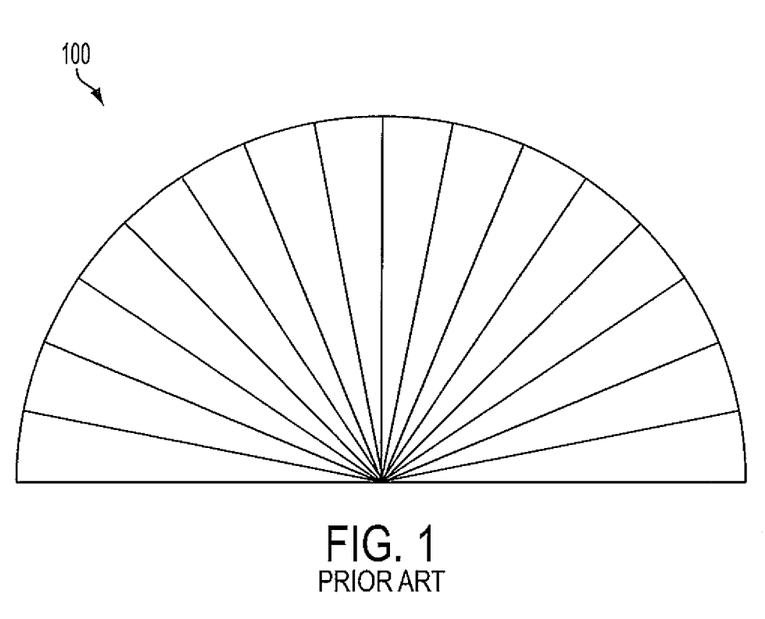
FIG. 1 is an illustration of a conventional subset using an Ordered Subset Expectation Maximization process.

Conventionally used subset algorithms utilize equidistant projections through the entire range of angles as shown in FIG. 1A. This scheme intuitively gives a maximum amount of azimuthal information per subset update. The algorithm updates the image through all of the subsets to obtain one iteration of the iterative process.

There remains a need in the art for improvement in image reconstruction techniques in order to increase accuracy and resolution.

BRIEF SUMMARY

A method and system is provided for performing medical imaging. The method and system includes at least one radiation detector to detect radiation from a subject, and an image processor which determines attenuation paths for an image point, groups substantially similar attenuation path lengths for the same image point to form a modified subset group, and processing image data using the modified subset group in order to provide a reconstructed image substantially similar to an original image.

Advantages will become more apparent to those skilled in the art from the following description of the preferred embodiments which have been shown and described by way of illustration. As will be realized, the system and method are capable of other and different embodiments, and their details are capable of modification in various respects. Accordingly, the drawings and description are to be regarded as illustrative in nature and not as restrictive.

BRIEF DESCRIPTION OF THE DRAWINGS

The present invention will become more fully understood from the detailed description given herein below and the accompanying drawings which are given by way of illustration only, and are not limitative of the present invention, and wherein.

DETAILED DESCRIPTION

Figure 2:
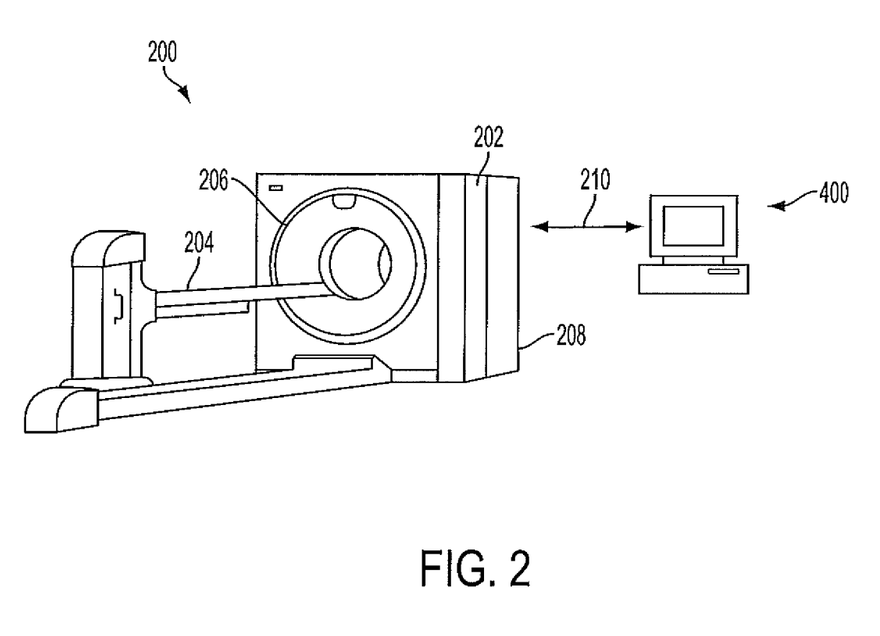
FIG. 2 illustrates an exemplary system for performing a modified subset process in accordance with an embodiment of the invention.

FIG. 2 is a system 200 for implementing the present invention in accordance with an embodiment of the present invention. Medical imaging system 200 may be comprised of a medical imaging device 202, i.e. a PET scanner, a SPECT, PET/MR scanner or any other device capable of acquiring a medical image. Medical imaging device 202 includes a pallet 204 for containing a patient (not shown). Detector 206 detects radiation emitted from the patient such as F-18, Tc-99m, Ga-67, and In-111. The processor 400 may be within the gantry 208 or detached from the gantry but connected via a data cable 210. Processor 400 receives and processes image data from medical imaging device 202. Processor 400 may have software running on it that executes a method of the present invention and outputs a fully three dimensional reconstruction of the object scanned using a modified subset scheme in accordance with an embodiment of the present invention.

Figure 3:
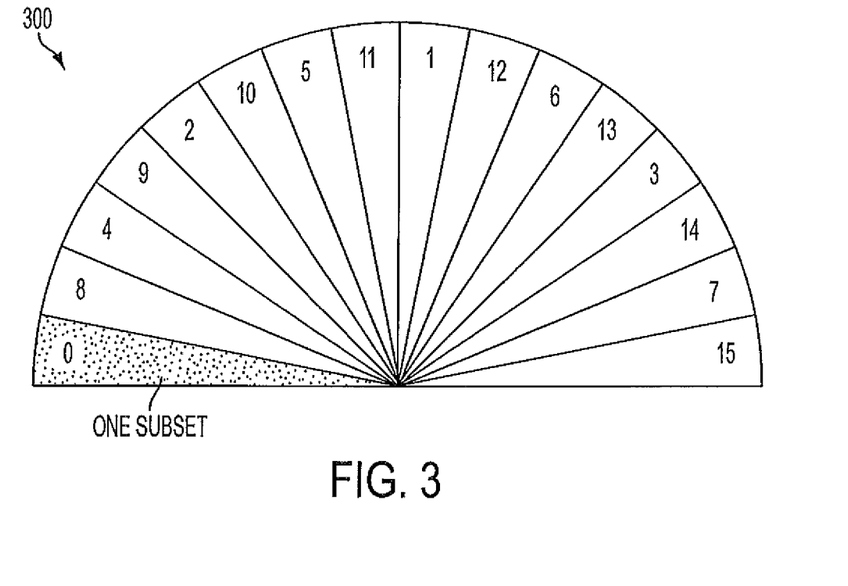
FIG. 3 illustrates a diagram depicting an exemplary subset configuration in accordance with an embodiment of the present invention.

The modified subset process groups the projections together to make a "pie" shape subset as seen in FIG. 3. This subset selection gives limited angle information rather than the sparse angle information that the conventional OSEM scheme provides. With the modified subset scheme, groupings are chosen as orthogonally spaced as possible. The implementation of this subset scheme is fairly straightforward and remains as flexible as the conventionally used OSEM process. Making the sequence of selection points as orthogonal as possible was found experimentally to be the most effective selection scheme in terms of convergence.

In accordance with an embodiment of the present invention, the modified subset method groups projections together where the attenuation paths for the same image point are all very similar with no extreme changes of attenuation path length. Specifically, attenuation paths are determined for an image point. Similar attenuation path lengths for the same image point are grouped to form a modified subset group. The modified subset group is used to reconstruct the image. Grouping the attenuation paths, results in the subsets having angles with similar weighting. The reconstruction then has similar confidence in the data across the subset when they are grouped together as opposed to having a large range of attenuating path lengths throughout a single subset. Nevertheless, the proposed scheme results in an image update closely related to limited angle tomography setup.

Block structure artifacts appear in images due to the subset number selection. This artifact is eliminated by selecting a subset number that is not a factor of the block periodicity. This artifact also tends to be lost in the noise past the first iteration and is not always seen in the case of typical scan counts. The source of the remaining artifacts could be attributed to the attenuation weighting in the system matrix and the method of the subset structure. When using the conventional method of creating a subset, the subset spans much of the angular range of projections. This creates projections that pass through differently attenuating paths in measured objects. For example, in a uniform elliptical shape, there are projections that will go through the maximum and minimum attenuating path. This results in significantly different measured values within these projections. Within the same subset, these higher counts in these projections will have more weight as they have less Poisson noise and the algorithm will try to model these projections first. This results in object elongation in the direction of the most statistically reliable projections. Only at later iterations the projections with less weight start being modeled after the larger weighted projection data are satisfied. At these iterations, the sphere will return to a more spherical shape but still won't be completely spherical. This conventional process is computational intensive.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 4:
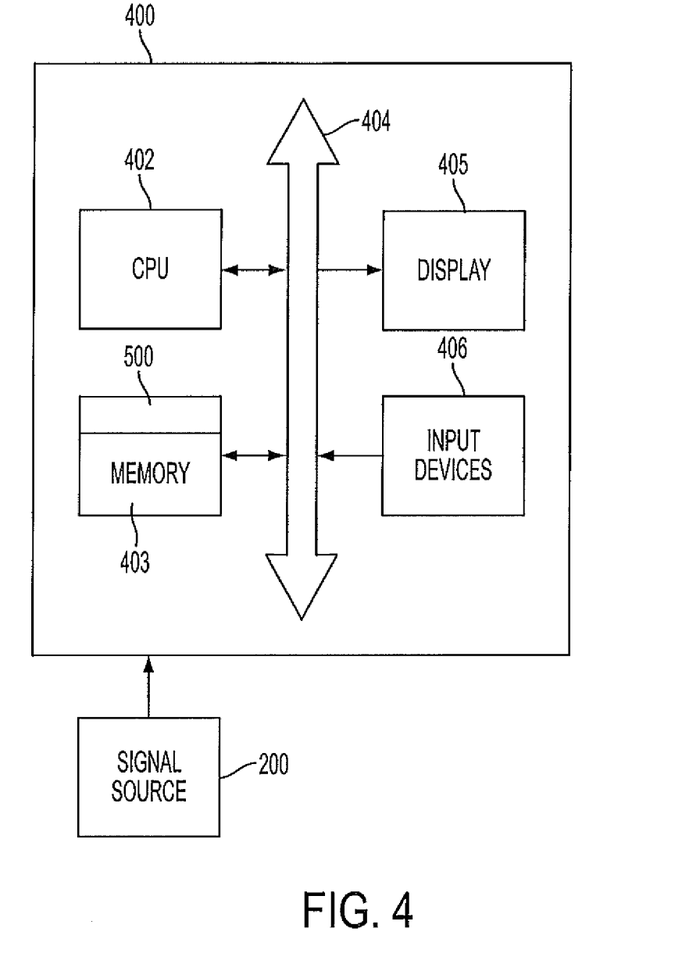
FIG. 4 illustrates a block diagram depicting an exemplary computer system for performing the modified subset process in accordance with an embodiment of the present invention.

Referring to FIG. 4, according to an embodiment of the present disclosure, a computer system 400 for implementing a method for extracting peak and grouping information, inter alia, a central processing unit (CPU) 402, a memory 403 and an input/output (I/O) interface 404. The computer system 400 is generally coupled through the I/O interface 404 to a display 405 and various input devices 406 such as a mouse and keyboard. The display 405 can display views of the reconstructed images. The support circuits can include circuits such as cache, power supplies, clock circuits, and a communications bus. The memory 403 can include random access memory (RAM), read only memory (ROM), disk drive, tape drive, etc., or a combination thereof. The present invention can be implemented as a routine 500 that is stored in memory 403 and executed by the CPU 402 to process the signal from the signal source such as system 200. As such, the computer system 400 is a general purpose computer system that becomes a specific purpose computer system when executing the routine 500 of the present invention.

The computer platform 400 also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Figure 5:
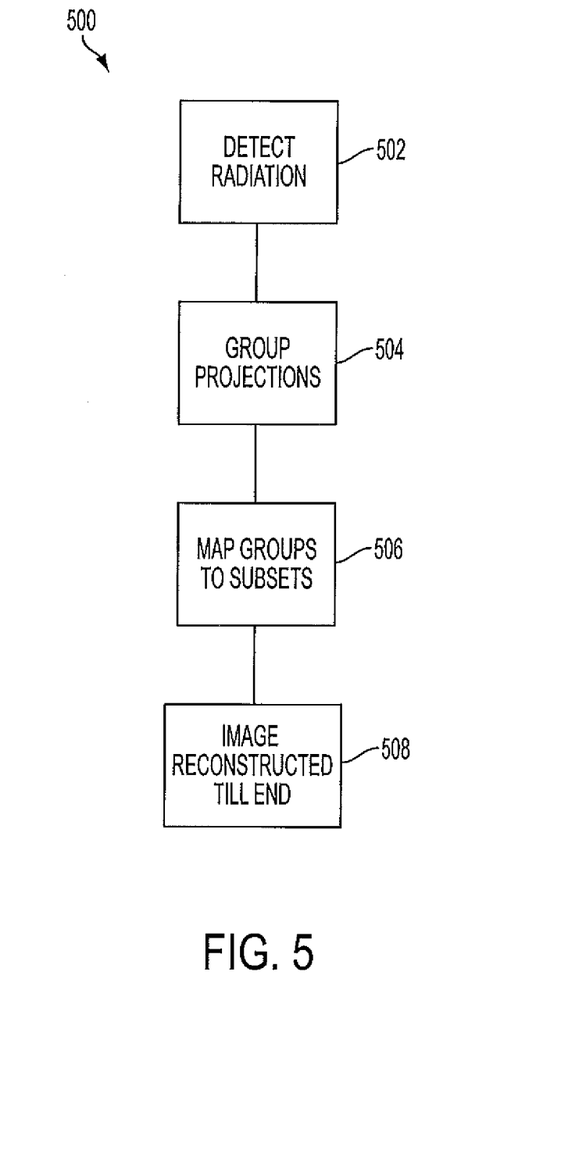
FIG. 5 illustrates a flowchart for performing the steps of an exemplary modified subset process in accordance with an embodiment of the present invention.

FIG. 5 is a flowchart of an embodiment of a method 500 for providing a modified subset in accordance with an embodiment of the present invention. The method 500 begins at step 502 with radiation being detected in a region of interest from medical imaging device 202. At step 504, the reconstruction process begins with projections being grouped together. That is attenuation paths for the same image point having lengths within a predetermined variance are grouped. The groups are then mapped to subsets at step 506. This results in the subsets having angles with similar weighing. At step 508, iterative reconstruction continues until the image is completed in accordance with an embodiment of the invention.

Figure 6A:
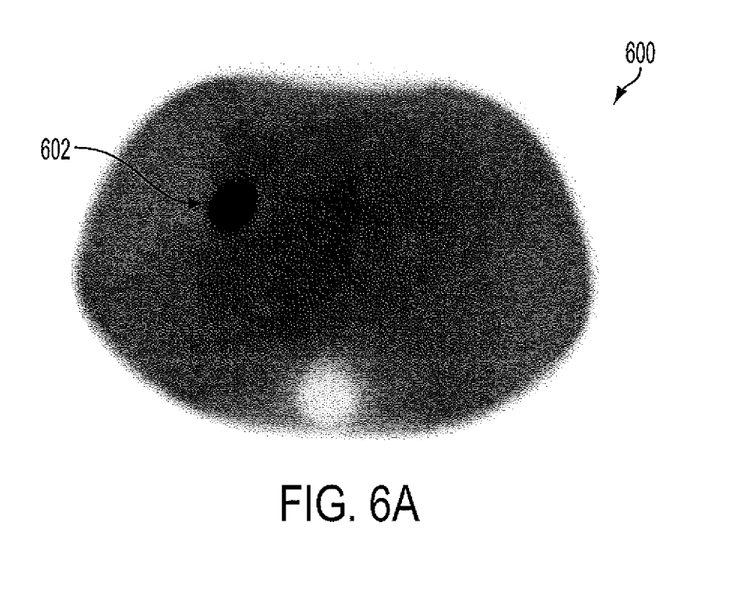
FIG. 6A illustrates an image depicting a transaxial view of a reconstructed image of a torso phantom reconstructed using the modified subset process in accordance with an embodiment of the present invention.
Figure 6B:
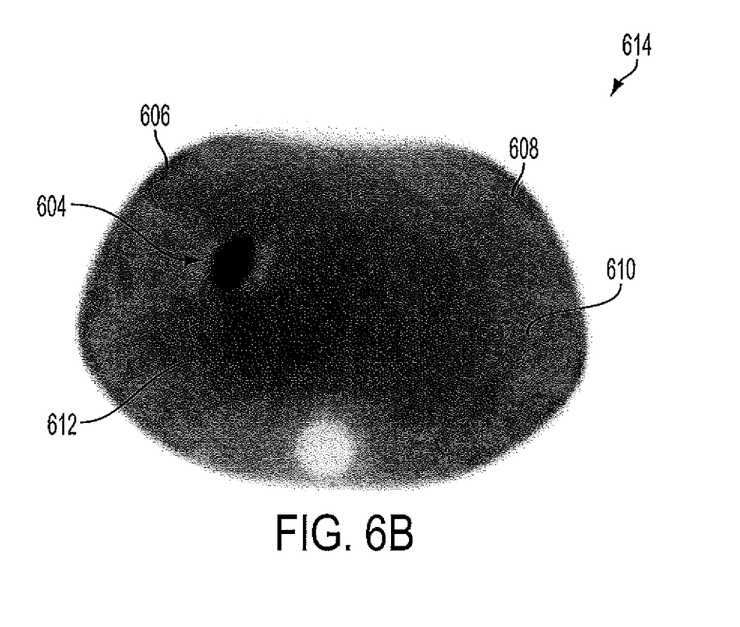
FIG. 6B illustrates an image depicting a transaxial view of a reconstructed image of the torso phantom reconstructed using the conventional OSEM process.

Several reconstructions were performed of a torso phantom (not shown) in order to evaluate any difference between the two subset schemes. OSEM was run for 3 iterations using 21 subsets. Images displayed are all of the first iteration as the artifacts are the strongest in this iteration and not lost in the increasing noise from later iterations. FIG. 6 shows a transaxial view of a uniform region that is located just above the liver in the torso phantom. The uniform region comprises an area between the top of the liver and below the lungs. In viewing FIG. 6A, it can be observed that there is a significant reduction of visible artifacts when using the modified subset algorithm. For example, hot spot 602 looks spherical. In addition, the image is sharper and does not have the blurriness of FIG. 6B.

FIG. 6B which depicts an image using a conventional OSEM algorithm shows the block structure periodicity artifact and the noise structure shown as rings 610 and 612 in the uniform background region. The dark hot spot 604 seen is the top of the liver and does exhibit a slight stretching in the vertical axis of the image. Artifacts can be seen along the edges of the image 606 and 608.

Figure 7A:
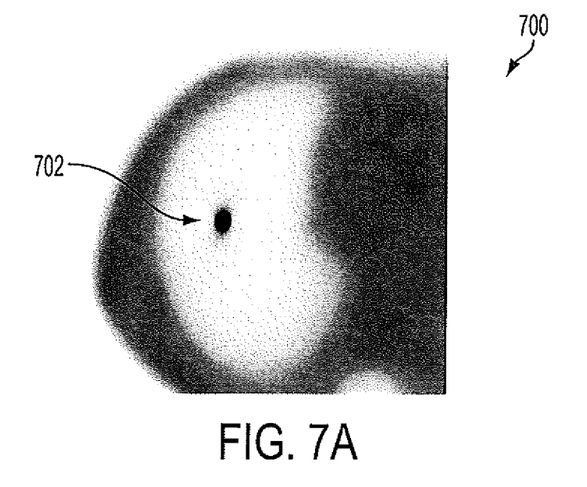
FIG. 7A illustrates an image depicting a transaxial view of a reconstructed image of a lung area of the torso phantom reconstructed using the modified subset process in accordance with an embodiment of the present invention.
Figure 7B:
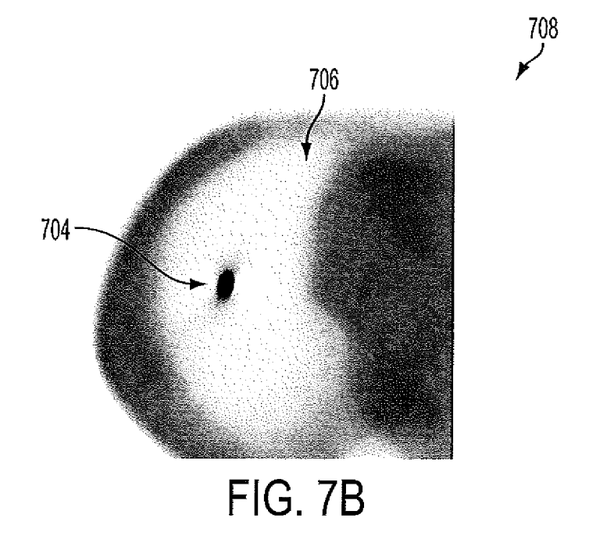
FIG. 7B illustrates an image depicting a transaxial view of a reconstructed image of the lung area of the torso phantom reconstructed using the conventional OSEM process.

FIG. 7 displays a hot sphere that is located in the lung of the torso phantom. FIG. 7A shows the result of the modified subset algorithm. The hot spot 702 looks much clearer than hot spot 704 in FIG. 7B. The image in FIG. 7B was created using the conventional OSEM algorithm. The stretching of the spherical region can be seen by hot spot 704. Also clearly visible in FIG. 7B is propagation of the cold region into the background regions of the image at the edge of the lungs as shown by cold spot 706. This is due to the same phenomena as the elongation of the spherical shape hot spots.

Figure 8A:
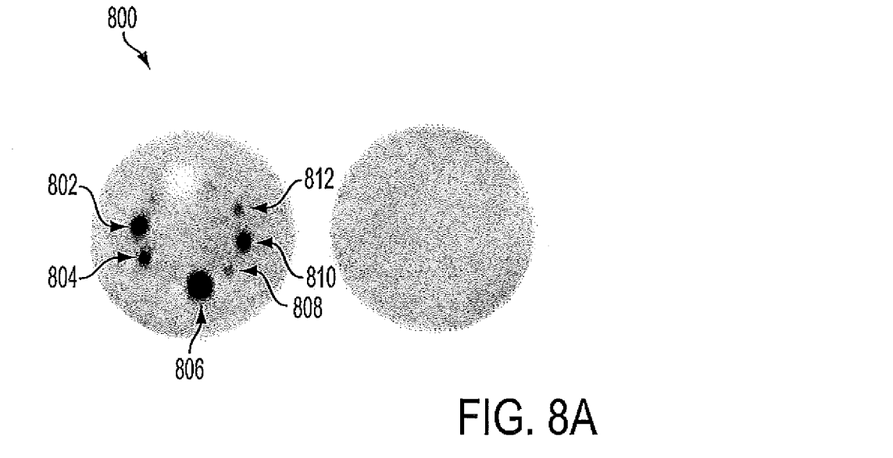
FIG. 8A illustrates an image depicting transaxial and axial views of a reconstructed image of the torso phantom reconstructed using the modified subset process in accordance with an embodiment of the present invention.
Figure 8B:
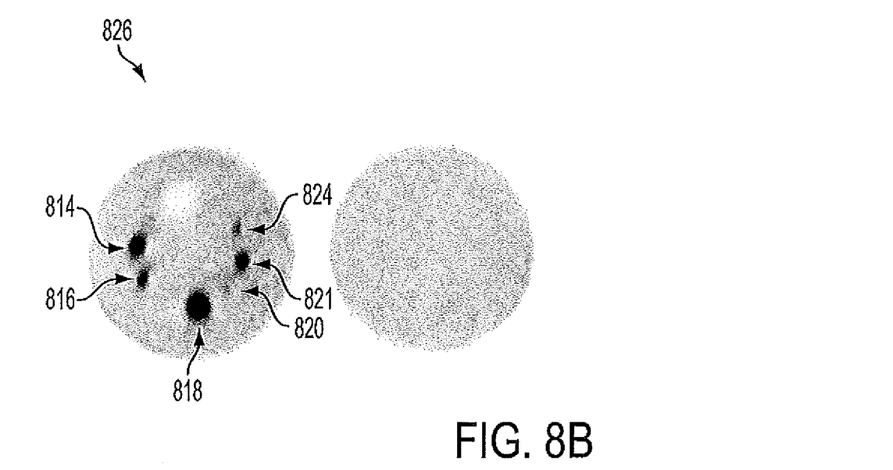
FIG. 8B illustrates an image depicting transaxial and axial views of a reconstructed image of the torso phantom reconstructed using the OSEM process with Time Of Flight (TOF) reconstruction.

Subset selection and its effects on time of flight reconstructions was also studied. The object used was an exemplary "T" phantom which comprised one 20 cm uniform phantom and one uniform phantom with hot spheres that were supported by a plastic support. The phantom had an exemplary horizontal dimension of 45 cm and an exemplary vertical dimension of 20 cm. The phantom was constructed as a representation of a human chest and characteristically has an almost 2:1 ratio of attenuating lengths in the extremes. The reconstruction performed was using time of flight with OSEM with 3 iterations and 24 subsets. FIGS. 8A and 8B show the resulting reconstructions after the first iteration. The reconstruction using the conventional OSEM algorithm exhibit distortions in hot sphere regions located off center of the object in FIG. 8B. There was also the ringing artifact in the noise structure. The ringing artifact was strong enough to propagate into the axial views of the image. The modified subset algorithm in FIG. 8A provided the geometrical recovery of the hot objects in the first iteration and eliminated the ringing as shown by the non-elongated hot spots 802, 804, 806, 808, 810 and 812. In FIG. 8B hot spots 814, 816, 818, 820, 822 and 824 are elongated and having ring artifacts.

Figure 9A:
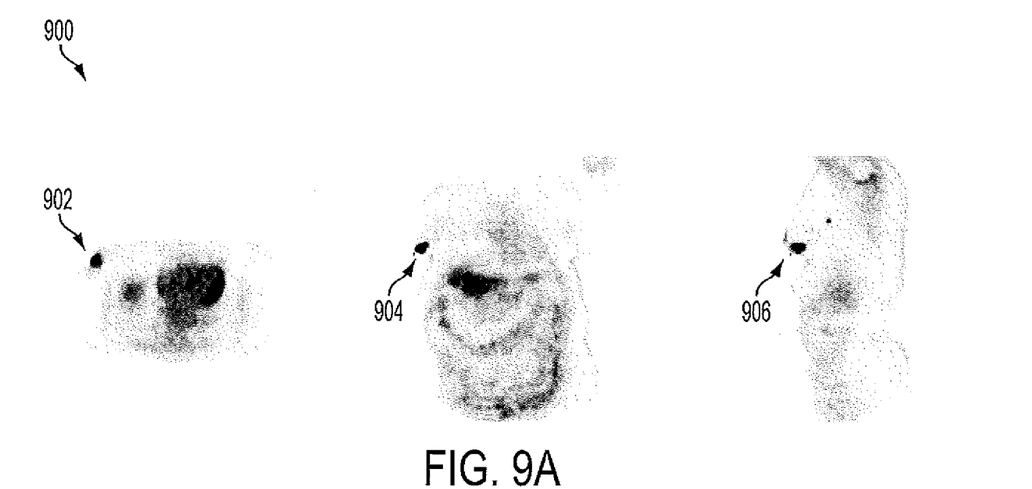
FIG. 9A illustrates an image depicting lesions in a reconstructed image of a breast area of the torso phantom reconstructed using the modified subset process in accordance with an embodiment of the present invention.

An additional study was performed on patient data to observe the effects of the subset scheme on irregular objects with similar artifacts observed in the images. These images were reconstructed using the conventional OSEM algorithm and the modified subset algorithm. Again, images shown and studied were of the first iteration of the reconstruction. When using the conventional OSEM algorithm, FIG. 9B reveals the ringing artifact observed in all phantom studies is present here too. For example, lesions 908, 910 and 912 are blurry and misshaped due to artifacts. In FIG. 9A, the ringing is suppressed and the background is more uniform using the modified subset algorithm as shown by lesions 902, 904 and 906.

Figure 9B:
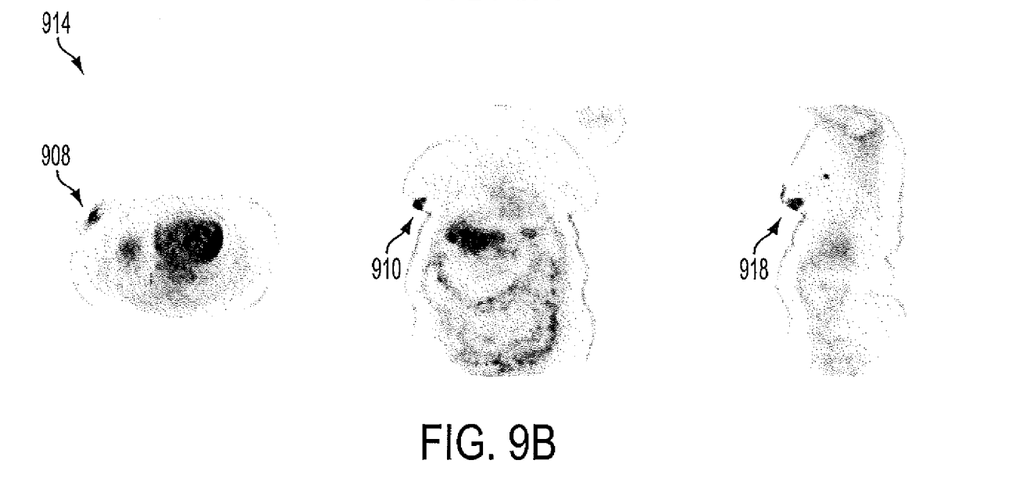
FIG. 9B illustrates an image depicting lesions in a reconstructed image of the breast area of the torso phantom reconstructed using the conventional OSEM process.

In this particular patient, there was an observed lesion at the edge of the patient's surface. It can be seen that the modified subset algorithm improves the reconstruction of the lesion 902 in the transaxial view. The lesion's geometry is recovered using the modified subset algorithm, where the conventional OSEM algorithm distorts the lesion 908. This distortion of the lesion results in voids in the image of the lesion in the axial views.

Modification of the subset selection schemes creates less artifacts then the conventional OSEM selection scheme when applied to attenuation weighted reconstruction algorithms. The shown results of the first iteration of these algorithms show that the convergence path is also changed by altering the subset selection schemes. This different convergence path results in fewer iterations needed to achieve the same image quality seen when using a higher number of iterations. The modified subset selection makes an improvement regardless of any additional improvement to the system modeling such as point spread function or time of flight of attenuation weighting algorithms. The modified subset scheme provides a reconstructed image that is substantially similar to the original image. The image has fewer artifacts than an image produced using the conventional OSEM algorithm.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

It is therefore intended that the foregoing detailed description be regarded as illustrative rather than limiting, and that it be understood that it is the following claims, including all equivalents, that are intended to define the spirit and scope of this invention.

What is claimed:

1. An imaging system comprising:
   at least one radiation detector to detect radiation from a subject; and
   an image processor which determines attenuation paths for an image point; groups substantially similar attenuation path lengths for the same image point to form a modified subset group; processes image data using the modified subset group in order to provide a reconstructed image substantially similar to an original image, and eliminates block artifacts by using a subset number that is not a factor of a block periodicity.

2. The system as set forth in claim 1, wherein the attenuation paths are grouped to form a pie shape subset.

3. The system as set forth in claim 2, wherein the subset provides limited angle information.

4. The system as set forth in claim 2, wherein subset groupings are orthogonally spaced.

5. The system as set forth in claim 1, wherein subset selection improves the image quality in objects with high activity regions that are located toward an edge of the object.

6. The system as set forth in claim 1, wherein attenuation paths amongst a subgroup are substantially similar.

7. The system as set forth in claim 1, the detector is part of at least one of: a PET scanner; a SPECT scanner; and a CT scanner.

8. A method of imaging using a processor comprising:
   detecting radiation from a subject;
   determining attenuation paths for an image point;
   grouping substantially similar attenuation path lengths for the same image point to form a modified subset group;
   processing image data using the modified subset group in order to provide a reconstructed image substantially similar to an original image; and
   eliminating block artifacts by using a subset number that is not a factor of a block periodicity.

9. The method as set forth in claim 8, further comprising: orthogonally spacing subset groupings.

10. The method as set forth in claim 8, wherein imaging is performed using at least one of a PET scanner; a SPECT scanner; and a CT scanner.

11. The method as set forth in claim 8, further comprising: forward projecting an estimate of reconstructed image data.

12. The method as set forth in claim 11, further comprising: backward projecting measured image data.

13. The method as set forth in claim 12, further comprising: determining a difference between forward projected image data and measured image data.

14. The method as set forth in claim 8, further comprising: determining that attenuation paths within a group are substantially similar.

15. The method as set forth in claim 8, further comprising: grouping the attenuation paths to form a pie shape subset.

16. The method as set forth in claim 8, wherein the subset provides limited angle information.

17. The method as set forth in claim 8, wherein subset selection improves the image quality in objects with high activity regions that are located toward an edge of the object.

18. The method as set forth in claim 8, wherein each subset includes attenuation paths having substantially similar angles and substantially similar weights.

* * * * *